US008952153B2

United States Patent
Aslan et al.

(10) Patent No.: US 8,952,153 B2
(45) Date of Patent: Feb. 10, 2015

(54) ONE POT PROCESS FOR PREPARING PEMETREXED DISODIUM

(71) Applicant: Kocak Farma Ilac ve Kimya Sanayi A. S., Uskudar, Istanbul (TR)

(72) Inventors: Tuncer Aslan, Istanbul (TR); Ender Kocak, Istanbul (TR)

(73) Assignee: Kocak Farma Ilac ve Kimya Sanayi A.S., Istanbul (TR)

( * ) Notice: Subject to any disclaimer, the term of this patent is extended or adjusted under 35 U.S.C. 154(b) by 0 days.

(21) Appl. No.: 14/352,671

(22) PCT Filed: Dec. 14, 2012

(86) PCT No.: PCT/TR2012/000213
§ 371 (c)(1),
(2) Date: Apr. 17, 2014

(87) PCT Pub. No.: WO2013/100872
PCT Pub. Date: Jul. 4, 2013

(65) Prior Publication Data
US 2014/0309420 A1 Oct. 16, 2014

(30) Foreign Application Priority Data

Dec. 29, 2011 (TR) ............................... a 2011 13223

(51) Int. Cl.
*A61K 31/519* (2006.01)
*C07D 487/04* (2006.01)

(52) U.S. Cl.
CPC ............ *C07D 487/04* (2013.01); *A61K 31/519* (2013.01)
USPC ........................................................ 544/280

(58) Field of Classification Search
None
See application file for complete search history.

(56) References Cited

U.S. PATENT DOCUMENTS

2010/0305319 A1   12/2010   Luo et al.

FOREIGN PATENT DOCUMENTS

| WO | 2008021405 | 2/2008 |
|----|------------|--------|
| WO | 2011019986 | 2/2011 |

OTHER PUBLICATIONS

International Search Report in International Application No. PCT/TR2012/000213 mailed on Apr. 23, 2013. (3 pages—see entire document).
Written Opinion of the International Searching Authority in International Application No. PCT/TR2012/000213 mailed on Apr. 23, 2013. (5 pages—see entire document).

*Primary Examiner* — Sun Jae Yoo
(74) *Attorney, Agent, or Firm* — Oppedahl Patent Law Firm LLC

(57) ABSTRACT

This invention relates to one pot process for preparing antifolate agent pemetrexed disodium in pure form.

9 Claims, No Drawings

ONE POT PROCESS FOR PREPARING PEMETREXED DISODIUM

This invention relates to one pot process for producing antifolate agent pemetrexed disodium in pure form.

Antifolate agents work by inhibiting the action of key enzymes thymidylate synthase and dihydrofolate reductase. Antifolates have found clinical utility as antitumor and antineoplastic agents. These agents inhibit both purine and pyrimidine synthesis by blocking enzyme functions and cause cell death. They have a greater toxic effect on rapidly dividing cell like cancer cells.

International Application Publication no WO 2011/019986 describes preparing well known potent folic acid antagonist pemetrexed and its related compounds. They carried out the reaction in an amide as solvent and observe that there are ten possible impurities which can form during the chemical sequence of the reaction.

U.S. Pat. No. 4,136,101 tells preparation of pemetrexed disodium starting from N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt by hydrolyzing with NaOH and isolating after pH adjustment. In the next step pemetrexed disodium was crystallized out from acetone/water to form heptahydarate. Although this approach seems good in the crystallization step a large amount of acetone must be used in a product/solvent ratio of 1 to 45 (w/v) which is not suitable for an industrial scale synthesis. In addition to that crystallization from acetone gives amorphous pemetrexed disodium.

US Application Publication no US 2010/0305319 A1 describes a method purifying salt of pemetrexed sodium in which a metal salt of pemetrexed is dissolved in water or optionally water-miscible organic solvent, water soluble metal salt was added and product was obtained by filtration after desalting. Again in this patent application firstly pemetrexed has to be isolated and then can be purified.

According to examples given above and other literatures present there is still a need to develop new efficient synthetic methods for the preparation of pemetrexed disodium.

For preparing drug substance the most important issue is purity and it affects directly the quality of drug product. As mentioned above pemetrexed disodium has many impurities which are process related or degradation products. So, it is much better to start to formulation with a pure drug substance. Different crystallization procedures were used to get pure pemetrexed disodium. For example, pemetrexed was crystallized out from a mixture of water/alcohol or using a mixture of two organic solvent such as methanol/dichloromethane. Up to now for purification process always a pemetrexed or its salt is first isolated and used as a starting material.

It has now been found that pure pemetrexed disodium can be directly obtained starting from dialkylester of pemetrexed or salts thereof.

In an aspect, the present application provides an efficient process for preparing pemetrexed or its metal salts starting from dialkyl esters of pemetrexed or salts thereof,
comprising:
a—dissolving or suspending dialkylester of pemetrexed or salts thereof in water or in a water/alcohol mixture
b—desalting and hydrolyzing ester moieties by using metal hydroxide
c—adding water soluble metal salts after pH adjustment; and
d—isolating pemetrexed salt from the mixture via filtration.

The dialkylester of pemetrexed can be chosen from the group consisting of methyl, ethyl, propyl, isopropyl esters and the like.

The salt of pemetrexed dialkyl ester can be chosen from the group consisting of p-toluensulfonate, benzenesulfonate, methanesulfonate and the like.

The water soluble metal salts can be chosen from the group consisting of sodium chloride, sodium bromide, sodium iodide and the like.

In a specific aspect the present application provides a one pot process for preparing pemetrexed disodium 2.5 hydrate in pure form
comprising:
a—suspending N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt in water
b—desalting and hydrolyzing it by using NaOH at a temperature from about 0 to 75° C.
c—precipitating pemetrexed disodium by adding NaCl after pH adjustment; and
d—isolating pemetrexed disodium from the mixture via filtration with a purity higher than 99.4%

It was now surprisingly found that pemetrexed disodium can be successfully obtained in one pot reaction in good yield with high purity Up to now metal salts of pemetrexed that used as drug substance can not be obtained in pure form following an efficient simple procedure.

When pemetrexed disodium was prepared and isolated following the simple procedure in this invention, the purity of the intermediate is higher than 99%. The hydrolysis reaction with pure intermediates gives pure pemetrexed in high yield.

It is yet an object of this invention is that N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt can be hydrolyzed under very mild basic conditions to give desired active substances or their salts in high yield with high analytical and optical purity.

Compounds of such a structure are known to show biological activity and therefore used as a anticancer drugs.

In an embodiment of the invention, the compound is a compound that shows antifolate activity and used treating different type of cancers. Pemetrexed disodium is particularly preferred.

The hydrolysis reaction is carried in a polar solvent, more preferably in water or in a water-alcohol mixture, alcohol selected from the group consisting of methanol, ethanol, propanol and isopropanol or mixtures thereof.

It has been shown that for this kind of reaction, particularly water gives the best results with regard to yield as well as solubility of the starting materials or their salts. After formation of metal salt of pemetrexed, water miscible sodium salt such as sodium chloride, sodium bromide, sodium iodide and the like can be added to reaction mixture and the pemetrexed metal salt is precipitated and isolated by filtration.

Precipitation is a particularly preferred method for isolating the formed pemetrexed or its salt since it can be affected by simply stirring the mixture at room temperature without the need for more complex purification technique such as column chromatography.

In a further embodiment of the invention, dialkylester of pemetrexed or salts thereof are hydrolyzed with the sodium hydroxide at a temperature from 0 to 75° C., preferably from 0 to 25° C.

The hydrolysis reaction is carried out in water or in water/alcohol, especially polar solvents give the best results with regard to yield as well as solubility of all agents involved.

Water and mixture of methanol, ethanol, propanol and isopropanol have thereby been shown to be the most suitable solvents at a temperature from 0° C. to 75° C., preferably from 0° C. to 25° C.

When water is used as a solvent in the hydrolysis reaction pemetrexed disodium directly precipitated from the reaction mixtures in a pH range about 5 to about 10, preferably in a pH range about 6 to about 9, especially pH about 8.0 at a temperature from 0 to 75° C., preferably from 0 to 25° C. after addition of sodium chloride.

It has been found that in the above-named temperature ranges, the reactions can be performed in 10 to 120 minutes, preferably 30 minutes for obtaining a good yield.

In a further embodiment of the invention, N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt is reacted with the metal hydroxide, to give pemetrexed disodium or its salt.

The hydrolysis reaction is carried out in a water/alcohol mixture in the presence of 1 to 5 equivalents, especially 3 equivalents of metal hydroxide, especially sodium hydroxide. Polar solvents give the best results with regard to yield as well as solubility of all agents involved.

It has been found that in the above-named time ranges a virtually complete hydrolysis reaction is achieved leading to high yields with high analytical and optical purity of pemetrexed or their pharmaceutically useful salts.

The salt form of the compounds of pemetrexed disodium is obtained by suspending N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt into water, hydrolyzing by using NaOH, adjusting the pH to about 8 with dilute HCl and then adding NaCl to the solution to precipitate.

It is understood that the above features and the features described below can be used not only in their described combination but also in other combinations or in isolation without departing from the scope of the invention.

The invention is now further illustrated by means of examples. These examples are not intended to limit the scope of the invention any way.

EXAMPLE 1

Preparation of pemetrexed disodium 2.5 hydrate starting from N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt A 500 mL flask equipped with magnetic stirrer, ice bath and thermometer was charged with 95 mL of water containing 1.52 g of NaOH (5 eqv.) and the solution was cooled to 0-5° C. To this solution was added 5 g of N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt. The mixture was stirred at 0-5° C. for 30-35 minutes. The pH was adjusted to 7-9 by adding 1N HCl. The mixture was warmed to rt. To the solution was added 10 gr of NaCl and stirred. At the beginning everything was dissolved and a clear solution was formed. The mixture was stirred at rt for 50-60 minutes and pemetrexed disodium was precipitated. The solid was isolated by filtration and washed with 10 ml of ethanol/water (7/2 v/v). The solid was dried in a vacuum oven at 50-55° C. for 5-6 hours to give 3.19 g of pemetrexed disodium 2.5 hydrate in 81% yield as a white solid with a purity of 99.5% analyzed by HPLC.

EXAMPLE 2

Preparation of pemetrexed disodium 2.5 hydrate starting from N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt A 3 L flask equipped with magnetic stirrer, ice bath and thermometer was charged with of 1 L of water containing 15.2 g of NaOH (5 eqv.) and the solution was cooled to 0-5° C. To this solution was added 50 g of N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt. The mixture was stirred at 0-5° C. for 30-35 minutes. The pH was adjusted to 7-9 by adding 1N HCl. The mixture was warmed to rt. To the solution was added 75 g of NaCl and stirred. At the beginning everything was dissolved and a clear solution was formed. The mixture was stirred at it for 50-60 minutes and pemetrexed disodium was precipitated. The solid was isolated by filtration and washed with 10 ml of ethanol/water (7/2 v/v). The solid was dried in a vacuum oven at 50-55° C. for 5-6 hours to give 32.7 g of pemetrexed disodium 2.5 hydrate in 83% yield as a white solid with a purity of 99.4% analyzed by HPLC.

The invention claimed is:

1. An efficient process for preparing pemetrexed or its metal salts starting from dialkylester of pemetrexed or salts thereof,
comprising:
dissolving or suspending dialkylester of pemetrexed or salts thereof in water or in a water/alcohol mixture;
desalting and hydrolyzing ester moieties by using metal hydroxide;
adding water soluble metal salts after pH adjustment; and
isolating pemetrexed salt from the mixture via filtration.

2. Process according to claim 1, wherein the solvent used is water or a water-alcohol mixture, and wherein the alcohol is selected from the group consisting of methanol, ethanol, propanol and isopropanol or mixtures thereof.

3. Process according to claim 1, wherein dialkylester of pemetrexed can be chosen from the group consisting of methyl, ethyl, propyl, and isopropyl.

4. Process according to claim 1, wherein salt of pemetrexed dialkyl ester can be chosen from the group consisting of p-toluensulfonate, benzenesulfonate, and methane sulfonate.

5. Process according to claim 1, wherein water soluble metal salts can be chosen from the group consisting of sodium chloride, sodium bromide, and sodium iodide.

6. Process according to claim 1, wherein pemetrexed disodium 2.5 hydrate is prepared in pure form,
comprising:
suspending N-[4-[2-(2-Amino-4,7-dihydro-4-oxo-3H-pyrrolo[2,3-d]pyrimidin-5-yl)ethyl]benzoyl]-L-glutamic acid diethylester p-toluenesulfonic acid salt in water;
desalting and hydrolyzing it by using NaOH at a temperature from about 0 to 75° C.;
precipitating p Disodium by adding NaCl after pH adjustment; and
isolating pemetrexed disodium from the mixture via filtration with a purity higher than 99.0%.

7. Process according to claim 1, wherein the hydrolysis is carried out at a temperature from 0 to 75° C.

8. Process according to the claim 7, wherein the hydrolysis reaction is carried out in water in the presence of 3 to 6 equivalents of sodium hydroxide.

9. Process according to claim 7, wherein the hydrolysis is carried out at a temperature from 0 to 25° C.

* * * * *